(12) United States Patent
Younger

(10) Patent No.: US 8,303,667 B2
(45) Date of Patent: Nov. 6, 2012

(54) FASTENING SYSTEM FOR PROSTHESES

(76) Inventor: Alastair Younger, Vancouver (CA)

( * ) Notice: Subject to any disclaimer, the term of this patent is extended or adjusted under 35 U.S.C. 154(b) by 160 days.

(21) Appl. No.: 12/716,097

(22) Filed: Mar. 2, 2010

(65) Prior Publication Data

US 2011/0218648 A1  Sep. 8, 2011

(51) Int. Cl.
*A61F 2/42* (2006.01)
(52) U.S. Cl. .................................... 623/21.18
(58) Field of Classification Search ............ 623/21.18
See application file for complete search history.

(56) References Cited

U.S. PATENT DOCUMENTS

| | | | |
|---|---|---|---|
| 3,987,500 A | 10/1976 | Schlein | |
| 4,021,864 A | 5/1977 | Waugh | |
| 5,163,961 A | 11/1992 | Harwin | |
| 5,226,917 A | 7/1993 | Schryver | |
| 5,360,452 A | 11/1994 | Engelhardt | |
| 5,766,259 A | 6/1998 | Sammarco | |
| 6,409,767 B1 | 6/2002 | Perice | |
| 6,663,669 B1 | 12/2003 | Reiley | |
| 2005/0125070 A1* | 6/2005 | Reiley ................ | 623/21.18 |
| 2006/0142870 A1 | 6/2006 | Robinson | |
| 2006/0229730 A1 | 10/2006 | Railey | |
| 2007/0142921 A1 | 6/2007 | Lewis | |
| 2008/0109081 A1 | 5/2008 | Bao | |
| 2008/0195233 A1 | 8/2008 | Ferrari | |

FOREIGN PATENT DOCUMENTS

| | | |
|---|---|---|
| EP | 1097680 B1 | 3/2000 |
| EP | 1435222 A1 | 7/2004 |
| WO | 9107931 A1 | 6/1991 |
| WO | 2005037135 A2 | 4/2005 |
| WO | 2006136940 A2 | 12/2006 |
| WO | 2008078082 A2 | 7/2008 |
| WO | 2009023666 A2 | 2/2009 |

OTHER PUBLICATIONS

The S.T.A.R. Scandanavian Total Ankle Replacement Patient Information brochure. Small Bone Innovations, Inc. 2009.

* cited by examiner

*Primary Examiner* — Bruce E Snow
(74) *Attorney, Agent, or Firm* — Berliner & Associates

(57) ABSTRACT

A system for fastening prosthetic implants such as ankle prostheses is provided. The ankle prosthesis includes: a talar implant having a body for mounting to a top of a talus and with at least one talar fastening hole; a tibial implant having a plate for mounting to a bottom of a tibia, a flange extending from the plate for bearing against an anterior surface of the tibia, the flange comprising at least one tibial fastening hole; a mobile bearing for positioning between the talar implant and the tibial implant; and a plurality of fasteners for locking engagement with the at least one talar fastening hole and the at least one tibial fastening hole, each of the fasteners comprising locking means and an elongated unthreaded body.

14 Claims, 17 Drawing Sheets

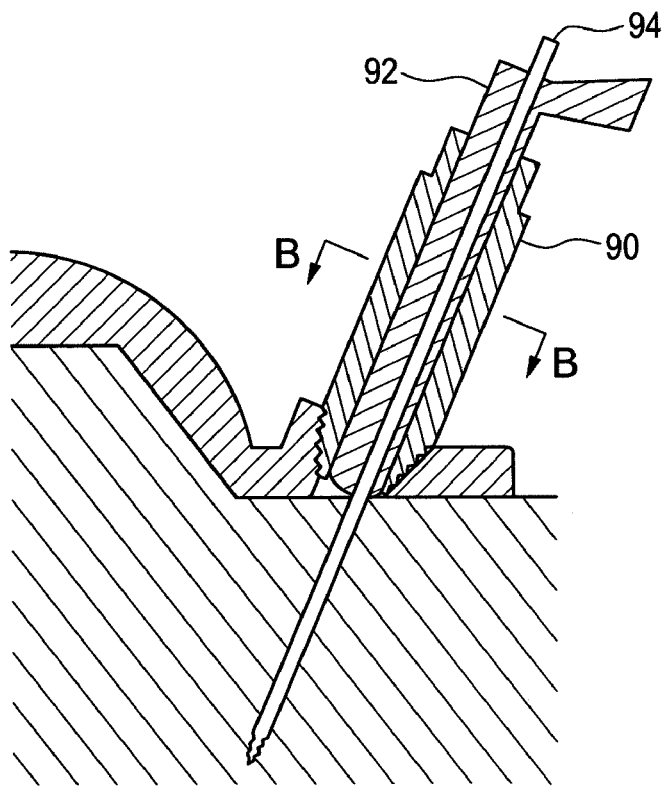
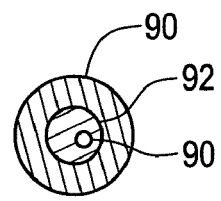
FIG. 33b
FIG. 33a
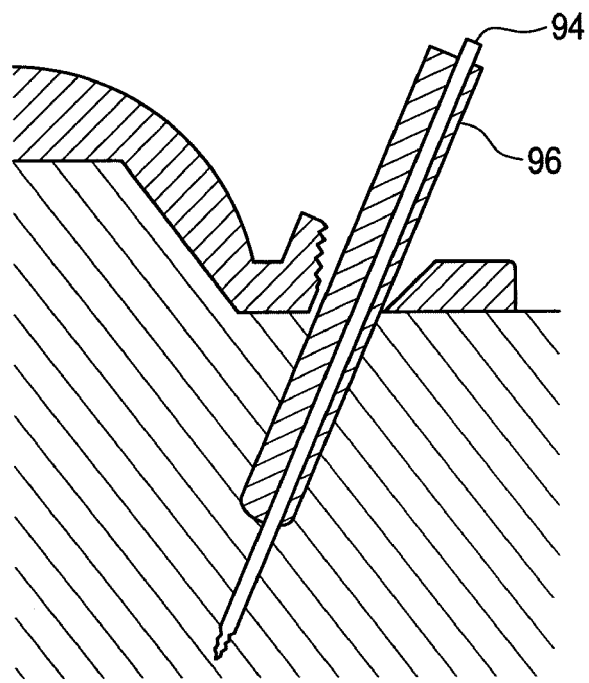
FIG. 34

FASTENING SYSTEM FOR PROSTHESES

TECHNICAL FIELD

This invention relates to prosthetic implants, and in particular to systems for fastening prosthetic implants such as ankle prostheses.

BACKGROUND

Cementless ankle prostheses for total ankle replacement surgeries are known. For example, the Scandinavian Total Ankle Replacement (S.T.A.R.®) system by Small Bone Innovations, Inc. is a three piece prosthesis including a talar component, mobile bearing and tibial component. Like many known systems, the S.T.A.R.® system relies on relatively large projections to fasten the prosthesis to bone. The S.T.A.R.® system, for example, features a fin on the talar implant that inserts caudally into a cut made in the talar dome, and two barrels oriented in the anterior/posterior direction on the tibial implant that insert into drilled holes in the tibia. Disadvantages of prostheses having relatively large projections include requiring a significant amount of bone removal and compromising blood supply in the bone.

Before an ankle prosthesis can be implanted, preparatory cuts in the talus and tibia must be made to facilitate positioning of the prosthesis. Typically, the preparatory cuts are not precisely complementary to the bone-contacting surfaces of the prosthesis. This imprecision may be due for example to differences in bone density across the section of the bone being cut. Imprecise preparatory cuts can result in imprecise fastening of the prosthesis to bone, leading to subsequent subsidence, loosening, and/or aseptic failure.

Also before implantation, a drilling template is typically placed over the pre-cut bone surface to guide the drilling of fastener holes in the bone surface. The drilling template is then removed, the actual prosthesis is positioned on the bone surface, and fasteners are inserted through the fastener holes of the prosthesis into the bone to fasten the prosthesis. Typically, however, the alignment of the drilling template on the bone is not identical to the alignment of the actual prosthesis on the bone, a difference due for example to the bone-contacting surface of the drilling template not corresponding precisely in profile to the bone-contacting surface of the prosthesis. The resulting misalignment between the drilled holes in the prepared bone surface and the holes in the actual prosthesis positioned on the prepared bone surface can also result in imprecise fastening of the prosthesis to bone. This misalignment can be further exacerbated by imprecise preparatory cuts in the bone as described above.

Cementless prosthetic implants that provide less intrusive but more precise and stable fastening to bone are therefore desired.

SUMMARY

According to one aspect of the invention, an ankle prosthesis is provided. The ankle prosthesis includes: a talar implant having a body for mounting to a top of a talus and with at least one talar fastening hole; a tibial implant having a plate for mounting to a bottom of a tibia, a flange extending from the plate for bearing against an anterior surface of the tibia, the flange comprising at least one tibial fastening hole; a mobile bearing for positioning between the talar implant and the tibial implant; and a plurality of fasteners for locking engagement with the at least one talar fastening hole and the at least one tibial fastening hole, each of the fasteners comprising locking means and an elongated unthreaded body.

The elongated unthreaded body of each of the fasteners may have a smooth surface, or a smooth surface and a non-smooth surface. The talar fastening hole and the tibial fastening hole may have internal threads. The locking means may be external threads on a head of each fastener for screw locking of each fastener to the talar fastening hole and the tibial fastening hole.

The talar fastening hole, the tibial fastening hole, and the head of each fastener may be frustoconical. The locking means may have a frustoconical head for taper locking of each fastener to the talar fastening hole and the tibial fastening hole.

The body of the talar implant may have an anterior flange extending from the body for bearing against a neck of the talus. The anterior flange has at least one talar fastening hole. The body of the talar implant may have an upper anterior surface having at least one talar fastening hole.

The ankle prosthesis may have two talar fastening holes and two tibial fastening holes. The talar fastening holes may be configured for vertical insertion of the fasteners and the tibial fastening holes may be configured for horizontal insertion of the fasteners. Or, the talar fastening holes may be configured for insertion of the fasteners at an acute posterior angle and the tibial fastening holes may be configured for insertion of the fasteners at an acute upward angle. The acute posterior angle may be substantially the same as the angle at which a posterior component of the body extends downward from the horizontal. The tibial fastening holes may be configured for insertion of the fasteners in a direction parallel to the medial border of the tibia in the transverse plane.

The talar fastening holes and tibial fastening holes may have a threaded arc section with internal threads, and an unthreaded arc section. At the distal end of the talar fastening holes and tibial fastening holes the radius of the unthreaded arc section is greater than a radius of the threaded arc section.

According to another aspect of the invention, a compression fastening system is provided. The system includes a plurality of fastening holes. Each fastening hole has a threaded arc section with internal threads, and an unthreaded arc section. The system also includes a plurality of fasteners for locking engagement with the fastening holes. Each of the fasteners has a head having external threads and an elongated unthreaded body.

The fastening holes and the head of the fasteners may be cylindrical, whereby a radius of the unthreaded arc section is greater than a radius of the threaded arc section to permit eccentric and gliding insertion of the fasteners in the fastening holes for compression locking.

The elongated unthreaded body may have a smooth surface and a non-smooth surface. The fastening holes and the head of the fasteners may be frustoconical, whereby a radius of a distal end of the unthreaded arc section is greater than a radius of the distal end of the threaded arc section to permit eccentric and gliding insertion of the fasteners in the fastening holes for compression locking.

According to another aspect of the invention, a talar implant for revision surgery or for bone loss surgery is provided. The talar implant has a dome-shaped body having an upper anterior surface and a substantially flat bottom surface, and at least one talar fastening hole extending in a downward and posterior direction from the upper anterior surface to the flat bottom surface. The ankle prosthesis also includes: a tibial implant; a mobile bearing for positioning between the talar implant and the tibial implant; and at least one fastener for locking engagement with the talar fastening hole, the fastener having locking means and an elongated unthreaded body. The elongated unthreaded body of the fastener may have a smooth surface and a non-smooth surface.

The talar fastening hole may have internal threads and the locking means may have external threads on a head of the fastener for screw locking of the fastener to the talar fastening hole.

The talar fastening hole and the head of the fastener may be frustoconical. The talar fastening hole may be frustoconical and the locking means may have a frustoconical head for taper locking of the fastener to the talar fastening hole.

According to another aspect of the a jig for drilling holes for prosthesis fasteners with a cannulated drill is provided. The jig includes: a prosthetic implant with a threaded fastener hole; a guide with a longitudinal bore and an externally threaded distal end for threadingly engaging the fastener hole; a cannula for insertion in the longitudinal bore of the guide, the cannula having an longitudinal bore; and a guidewire for insertion in the longitudinal bore of the cannula, the guidewire guiding the cannulated drill. The longitudinal bore of the cannula or the guide may be eccentric. The distal end of the guide may be frustoconical. The guide may have a slotted proximal end for engagement with a T-handle.

According to another aspect of the invention, a method of fastening a prosthesis to bone is provided. The method includes the steps of:
  (a) precutting the bone to provide a bone surface complementary to a bone-contacting surface of the prosthesis;
  (b) positioning the prosthesis on the bone surface;
  (c) implanting a threaded guidewire into a location of bone through a fastening hole of the prosthesis positioned on the bone;
  (d) drilling a drill hole in the bone through the fastening hole using a cannulated drill guided by the threaded guidewire;
  (e) inserting through the fastening hole and into the drill hole a fastener comprising a locking head and an unthreaded elongated body; and
  (f) locking the head of the fastener in the fastening hole to fasten the prosthesis to the bone.

Step (b) may involve overdrilling the drill hole to prevent the fastener from backing out of the drill hole. In step (b) the diameter of the drill hole may be less than the diameter of the unthreaded elongated body of the fastener, so the drill hole by scratch fit. Step (c) may include implanting the threaded guidewire eccentric in relation to the fastening hole. Step (d) may include drilling the drill hole eccentric in relation to the fastening hole. Step (f) may include pulling the prosthesis in a direction corresponding to the eccentricity of the drill hole.

BRIEF DESCRIPTION OF DRAWINGS

In drawings which show non-limiting embodiments of the invention:

FIGS. 33A to 36 are cutaway side views illustrating the steps in fastening an implant to bone according to one embodiment of the invention (FIG. 33*b* is a cross sectional view along plane B-B in FIG. 33*a*);

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Throughout this specification, the terms "proximal" and "distal" refer to positions respectively closer to and further from the surgeon.

Figure 1:
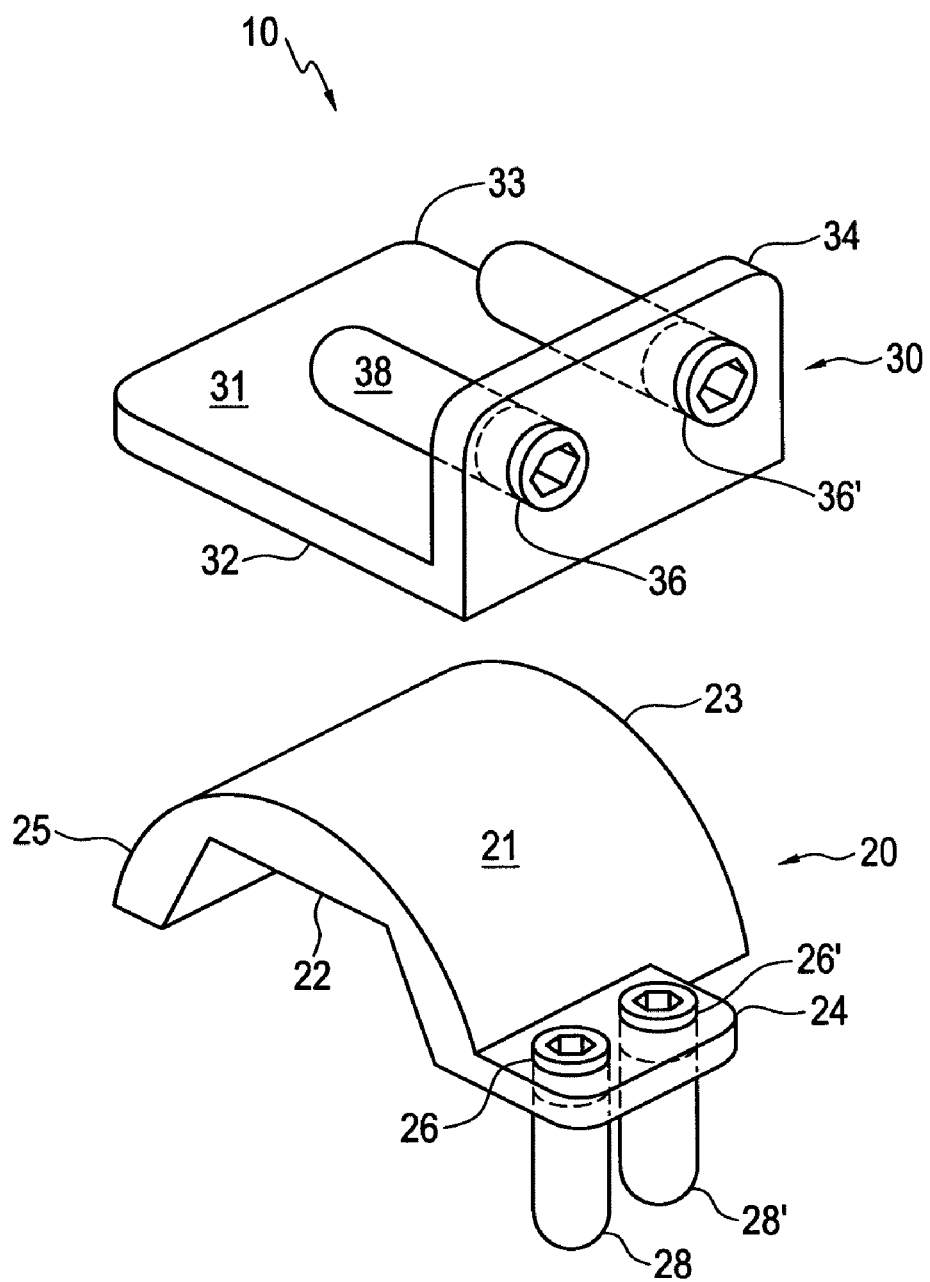
FIG. 1 is a perspective view of an ankle prosthesis according to one embodiment of the invention.
Figure 2:
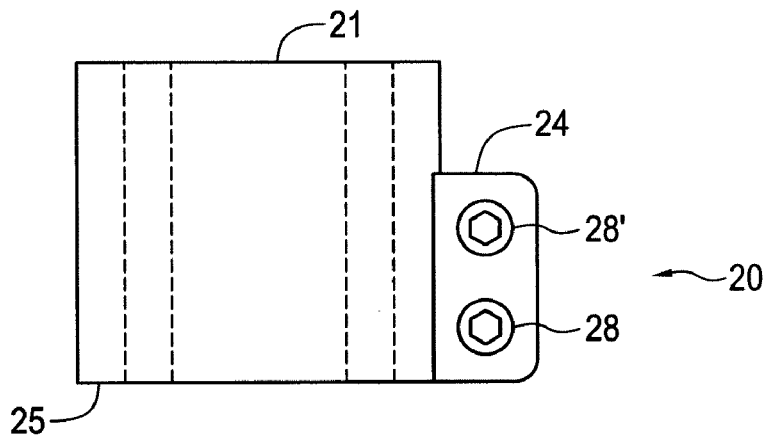
FIG. 2 is a top view of the talar implant of the embodiment illustrated in FIG. 1.
Figure 3:
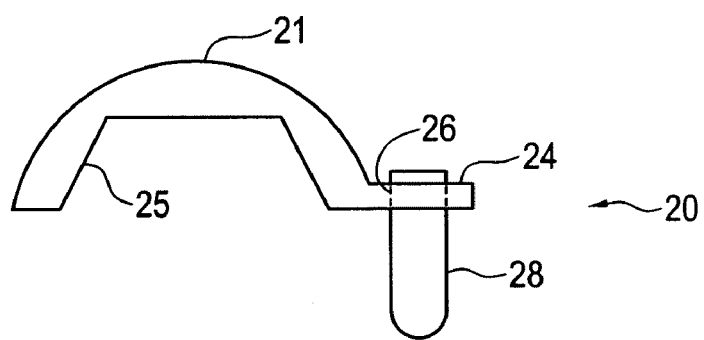
FIG. 3 is a side view of the talar implant of the embodiment illustrated in FIG. 1.
Figure 4:
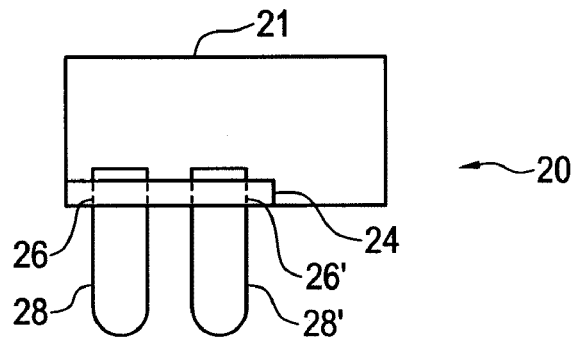
FIG. 4 is a front view of the talar implant embodiment illustrated in FIG. 1.
Figure 5:
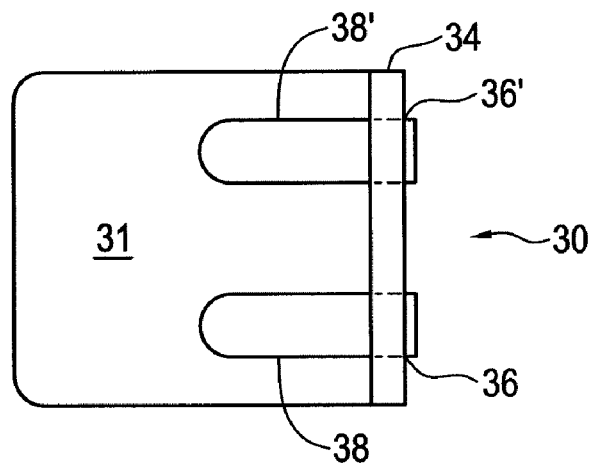
FIG. 5 is a top view of the tibial implant of the embodiment illustrated in FIG. 1.
Figure 6:
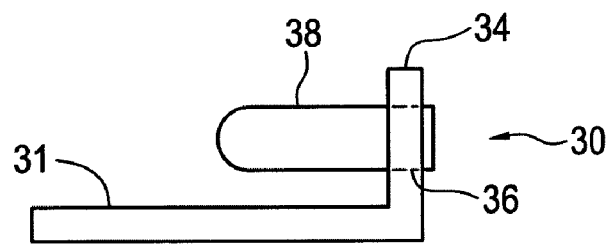
FIG. 6 is a side view of the tibial implant of the embodiment illustrated in FIG. 1.
Figure 7:
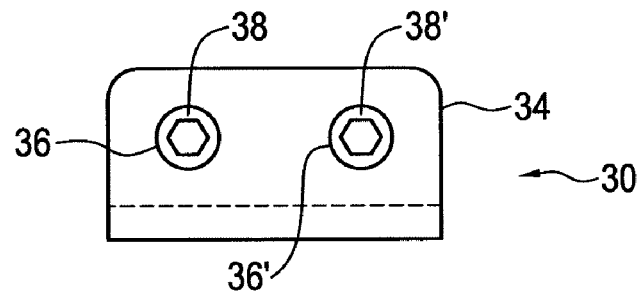
FIG. 7 is a front view of the tibial implant of the embodiment illustrated in FIG. 1.
Figure 8:
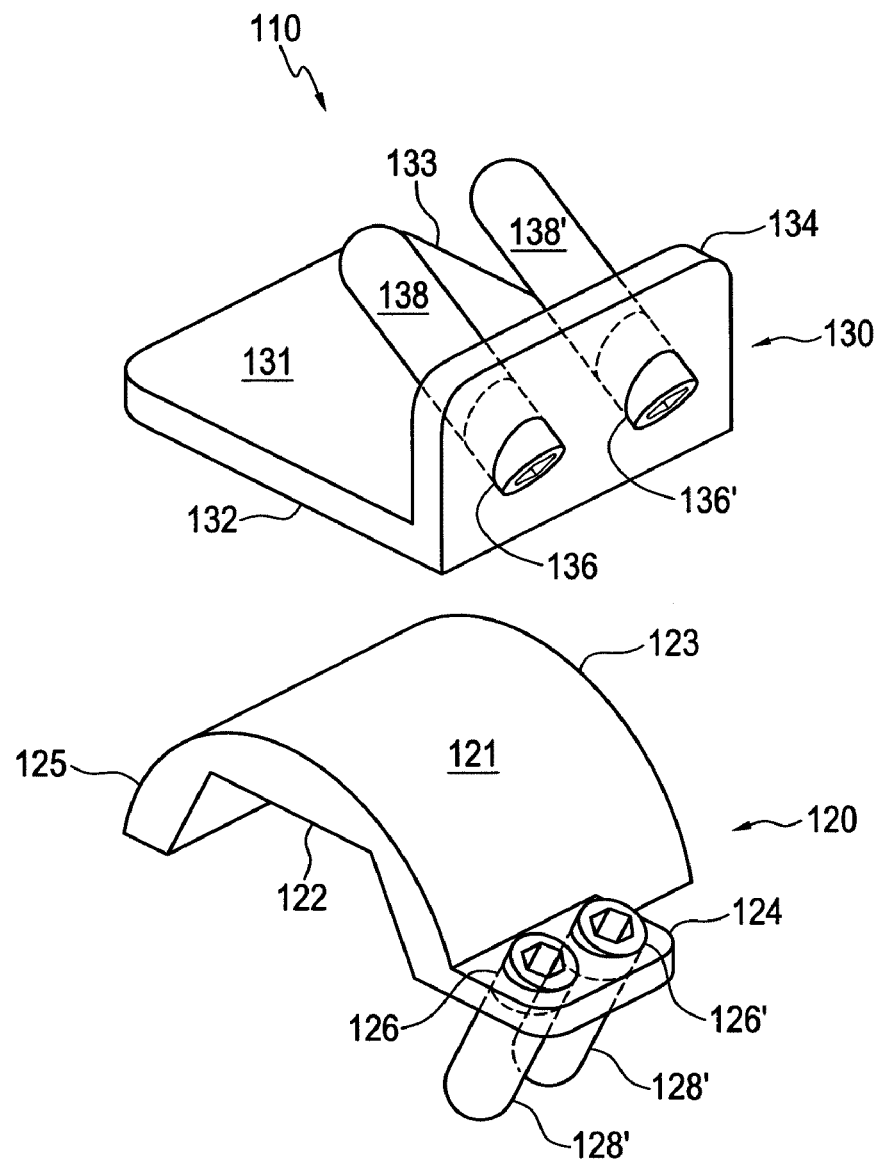
FIG. 8 is a perspective view of an ankle prosthesis according to one embodiment of the invention.
Figure 9:
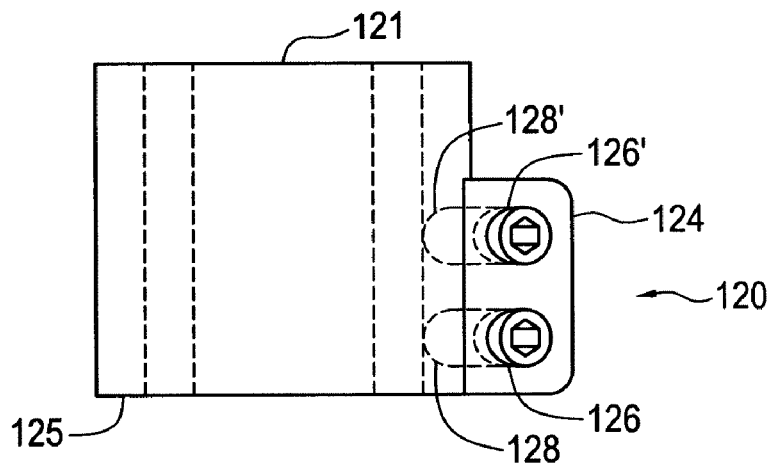
FIG. 9 is a top view of the talar implant of the embodiment illustrated in FIG. 8.
Figure 10:
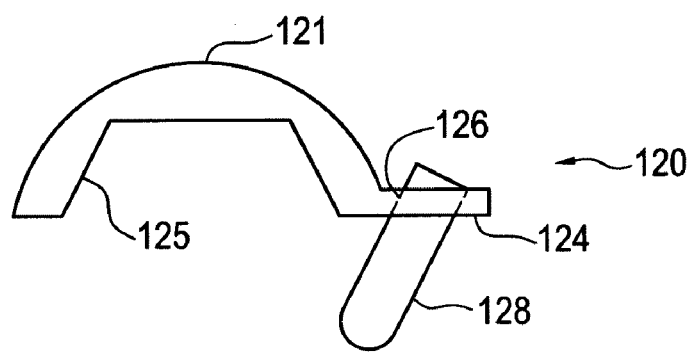
FIG. 10 is a side view of the talar implant of the embodiment illustrated in FIG. 8.
Figure 11:
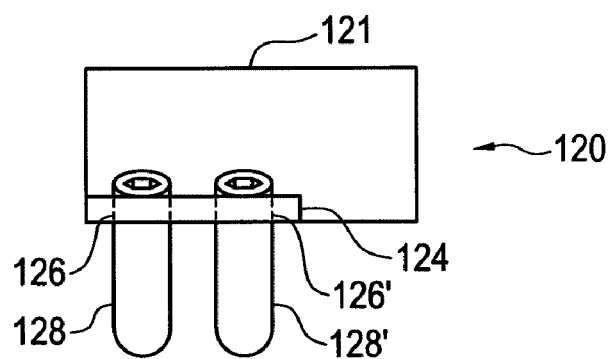
FIG. 11 is a front view of the talar implant embodiment illustrated in FIG. 8.
Figure 12:
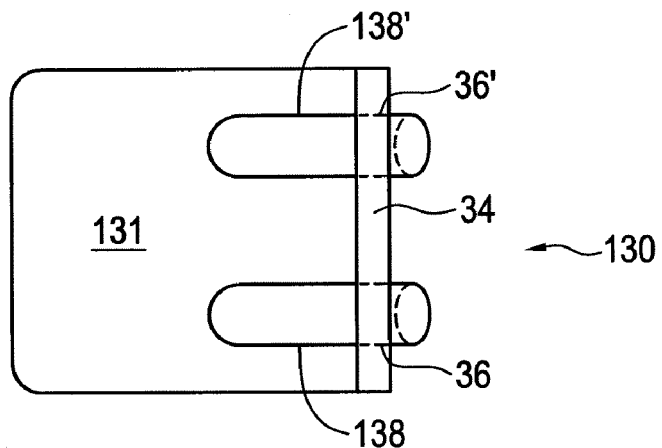
FIG. 12 is a top view of the tibial implant of the embodiment illustrated in FIG. 8.
Figure 13:
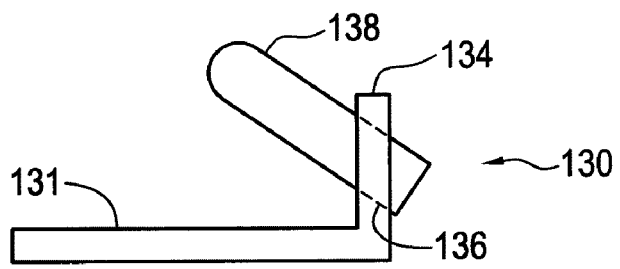
FIG. 13 is a side view of the tibial implant of the embodiment illustrated in FIG. 8.
Figure 14:
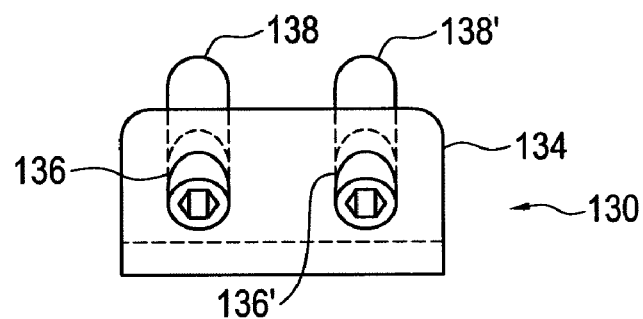
FIG. 14 is a front view of the tibial implant of the embodiment illustrated in FIG. 8.

FIG. 1 shows a left ankle prosthesis 10 according to one embodiment of the present invention. A right ankle prosthesis according to this embodiment would be a mirror image of left ankle prosthesis 10. Ankle prosthesis 10 is a cementless three-piece ankle prosthesis that includes a talar implant 20 for fastening to the talar dome, a tibial implant 30 for fastening to the bottom of the tibia, and a mobile bearing (not shown) moveable between the talar implant 20 and tibial implant 30. Talar implant 20 and tibial implant 30 may be made of medical grade metal (e.g. titanium) and/or metal alloy (e.g. chromium/cobalt), or other similar bio-compatible materials. The mobile bearing may be made of medical grade ceramic, plastic (e.g. ultra high molecular weight polyethylene) or other similar bio-compatible materials.

As shown in FIGS. 1 to 4, talar implant 20 has a generally C-shaped body 21 with a bottom surface 22 and a top surface 23. In other embodiments body 21 may be dome-shaped. Bottom surface 22 is concave and shaped to fit over the talar dome. Bottom surface 22 may be provided with a coating to accelerate bone ingrowth for aiding fixation. The talar dome may be pre-cut to provide a complementary surface for registering with bottom surface 22. In the illustrated embodiment, for example, the talar dome would have a trapezoidal cut on top of which bottom surface 22 would register. Bottom surface 22 may be provided with one or more spikes (not shown) for anchoring talar implant 20 to the talus. Top surface 23 is in free frictional sliding contact with a complementary shaped bottom surface of the mobile bearing.

Body 21 may include a flange 24 that extends forward from the medial side of the anterior end of body 21. Flange 24 is configured to rest substantially flat against the neck of the talus. The neck of the talus may be pre-cut to provide a flat surface for flange 24 to rest against.

In the illustrated embodiment, posterior portion 25 of implant 20 extends downward to about the plane of flange 24. In other embodiments, posterior portion 25 may not extend as far downward as, or may extend further downward below, the plane of flange 24.

Flange 24 includes fastening holes 26, 26'. As described further below, fasteners 28, 28' are locked vertically in fastening holes 26, 26' after insertion into underlying bone tissue to fasten talar implant 20 to the talus.

As shown in FIGS. 1 and 5 to 7, tibial implant 30 has a plate 31 having a bottom surface 32 and a top surface 33. Plate 31 extends along the sagittal length of the tibia and bears against the lateral portion of the lower end of the tibia. Bottom surface 32 is in free frictional sliding contact with a complementary shaped top surface of the mobile bearing. Top surface 33 may be provided with a coating to accelerate bone ingrowth from the lower end of the tibia to aid fixation. The lower end of the tibia may be pre-cut to provide a flat surface for plate 31 to bear against. A flange 34 extends upwards from the anterior end of plate 31. Flange 34 includes fastening holes 36, 36'. Fasteners 38, 38' are locked horizontally in fastening holes 36, 36' after insertion into underlying bone tissue to fix tibial implant 30 to the tibia. Fasteners 38, 38' may oriented parallel to the medial border of the tibia in the transverse plane.

FIGS. 8-14 shows ankle prosthesis 110 according to another embodiment of the present invention. Ankle prosthesis 110 has features identical to ankle prosthesis 10 except that for both talar implant 120 and tibial implant 130, the fastening holes are designed for angled insertion of fasteners. Unless otherwise stated, the angles of the fasteners as discussed in this specification relate to angles in the sagittal plane. For talar implant 120, fasteners 128, 128' are locked in fastening holes 126, 126' in flange 124 at an acute angle in the posterior direction. The angle at which fasteners 128, 128' penetrate the talus may be parallel to the angle of posterior extension 125 of body 121. For tibial implant 130, fasteners 138, 138' are locked in fastening holes 136, 136' at an upward angle in the posterior direction. Angled upward insertion of fasteners 138, 138' allows the fasteners to be anchored in the compact bone of the diaphysis of the tibia, resulting in more secure fastening compared to horizontal insertion of the fasteners into the spongy bone of the epiphysis of the tibia.

Figure 37:
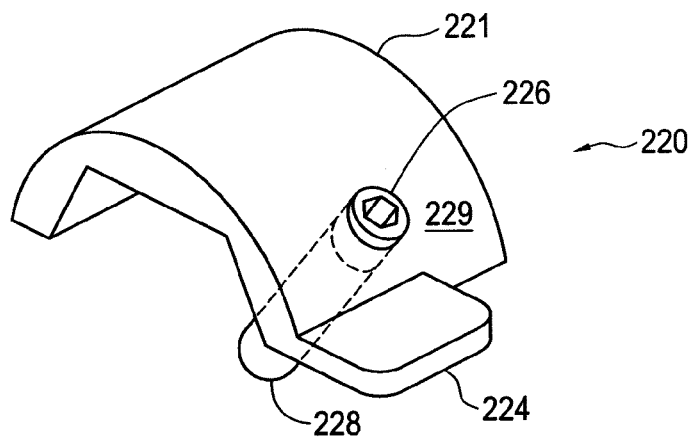
FIG. 37 is a perspective view of a talar implant according to one embodiment of the invention.
Figure 38:
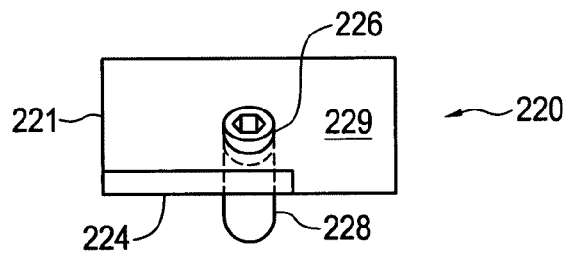
FIG. 38 is a front view of the talar implant illustrated in FIG. 37.
Figure 39A:
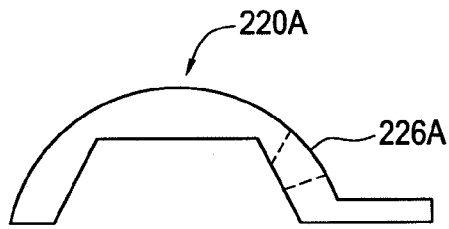
FIGS. 39A and 39B show examples of talar imp, namely talar implants 220A, 220B having taper lock fastening hole 226A and screw lock fastening hole 226B respectively.
Figure 39B:
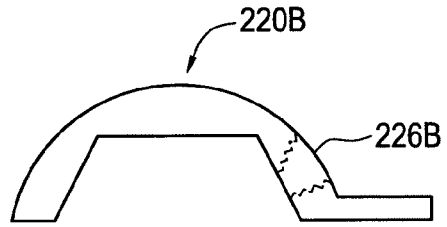

FIGS. 37 and 38 show another embodiment of the present invention where talar implant 220 is provided with at least one fastening hole 226 for receiving fastener 128 in an upper anterior face 229 of body 221 at an acute angle. Body 221 may be C-shaped or dome-shaped with a concavity, for example. Fastener 228 and fastening hole 226 correspond in form and function to fasteners 128, 128' and fastening holes 126, 126' of talar implant 120. In some embodiments, such as the one illustrated in FIGS. 37 and 38, talar implant 220 may have an anterior flange 224, and anterior flange 224 may be provided with at least one fastening hole (not shown) for receiving at least one fastener as described above for talar implants 20, 120. Upper anterior surface 229 may not articulate with the mobile bearing. FIGS. 39A and 39B show examples of talar implant 220, namely talar implants 220A, 220B having taper lock fastening hole 226A and screw lock fastening hole 226B respectively.

Figure 40:
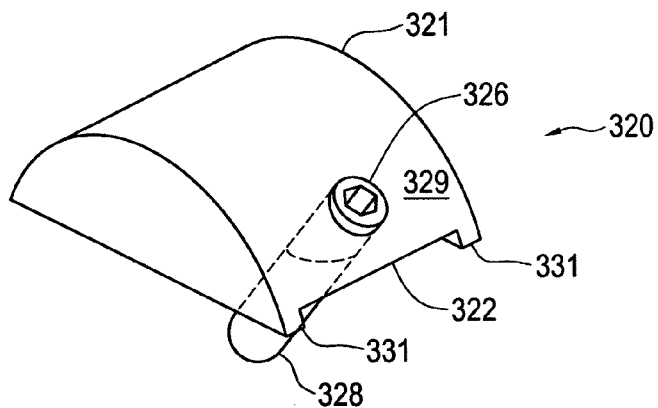
FIGS. 40 to 42B are various views of an embodiment of a talar dome.
Figure 41:
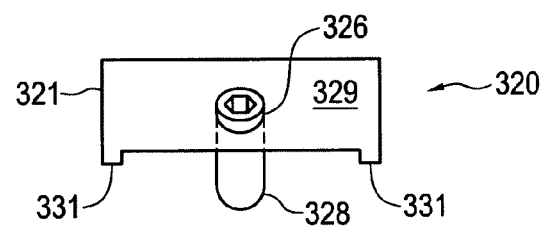
Figure 42A:
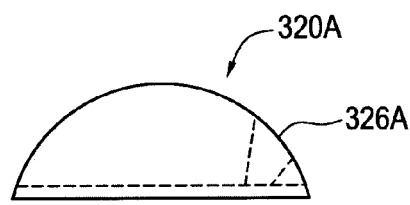
Figure 42B:
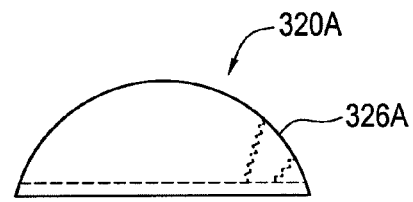

In other embodiments, the talar implant could be provided in a modified form for bone loss and revision surgeries. Instead of a C-shaped body or a dome-shaped body with a concavity, the talar implant may be provided as a solid dome having a base to bear against a pre-cut portion of the talar dome as shown in FIGS. 40 and 41. Talar implant 320 shown in FIG. 40 has a solid dome-shaped body 321 with a substantially flat bottom surface 322. By "substantially" flat bottom surface it is understood that bottom surface 322 may, in some embodiments, be completely flat, while in other embodiments may have, for example, one or more small projections (e.g. spikes) or indentations to facilitate fastening of the implant to bone or facilitate registration between the implant and bone. At least one fastener hole 326 receives at least one fastener 328 at an acute angle through an upper anterior surface 329 of body 321 to bottom surface 322 so that fastener 328 penetrates through body 321 to fasten talar implant 320 to bone. In some embodiments, talar implant 320 may have an anterior flange (not shown) provided with at least one fastening hole for receiving at least one fastener as described above for talar implants 20, 120. Upper anterior surface 329 may not articulate with the mobile bearing. As shown in FIG. 41, talar implant 320 may be provided with lateral guide rails 331 extending in the anterior/posterior direction to facilitate positioning of talar implant 320 on the pre-cut talus bone. FIGS. 42A and 42B show examples of talar implant 320, namely talar implants 320A, 320B having taper lock fastening hole 326A and screw lock fastening hole 326B respectively.

Figure 15:
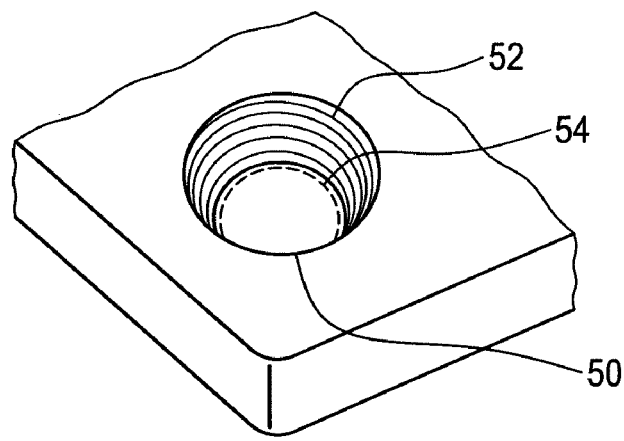
FIG. 15 is a perspective view of a fastening hole according to one embodiment of the invention.
Figure 16:
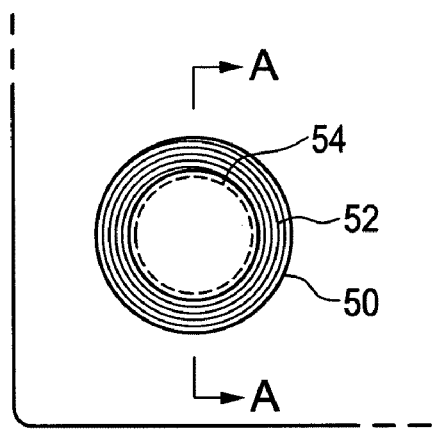
FIG. 16 is a top view of the fastening hole illustrated in FIG. 15.
Figure 17:
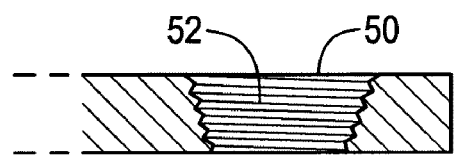
FIG. 17 is a side view along plane A-A in FIG. 16.

FIGS. 15 to 17 show fastening hole 50, an example embodiment of fastening holes 26, 26', 36 and 36'. Fastening hole 50 is configured for "neutral" locking of a fastener. Fastening hole 50 is frustoconical (as best shown in FIG. 17) and has internally spiralling threads 54 for receiving a frustoconical threaded head of a fastener. As described below, drill hole 58 must be made in the underlying bone before the fastener can be inserted. Drill hole 58 is centered with respect to fastening hole 50. The diameter of drill hole 58 may be somewhat less than the diameter of the fastener to provide an interference or "scratch" fit. In other embodiments, the diameters of the drill hole and fastener may be substantially the same. The fastener is locked in as the thread of the fastener head is threaded into fastening hole 50.

Figure 18:
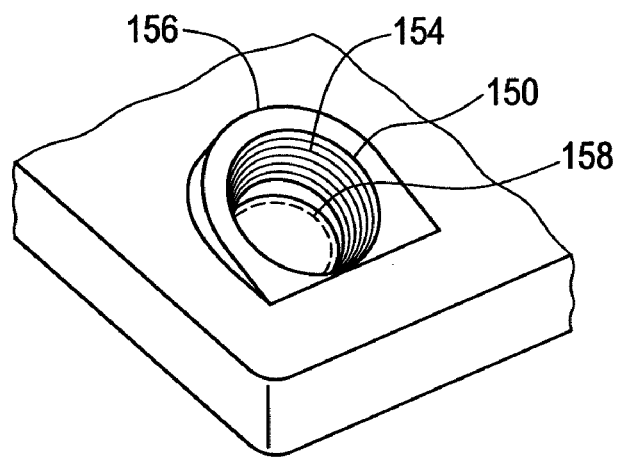
FIG. 18 is a perspective view of a fastening hole according to one embodiment of the invention.
Figure 19:
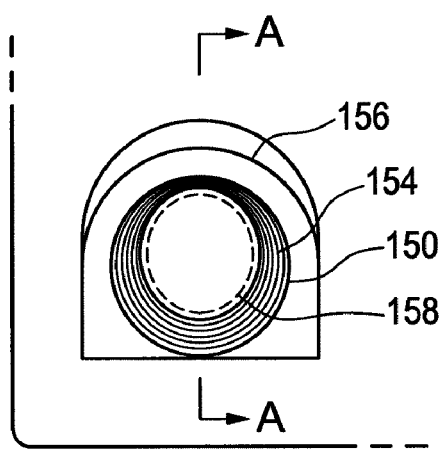
FIG. 19 is a top view of the fastening hole illustrated in FIG. 18.
Figure 20:
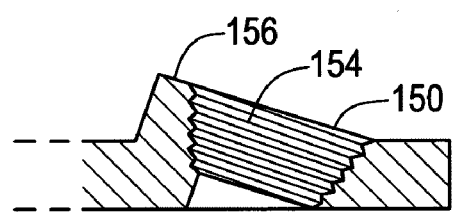
FIG. 20 is a side view along plane A-A in FIG. 19.

FIGS. 18 to 20 show fastening hole 150, an example embodiment of fastening holes 126, 126', 136, 136', 226, and 326. Fastening hole 150 is configured for neutral locking of a fastener at an acute angle to the face of the implant. Fastening hole 150 is frustoconical and has internally spiralling threads 154. Drill hole 158 made in the underlying bone is centered with respect to fastening hole 150. Like drill hole 58, the diameter of drill hole 158 may be somewhat less than the diameter of the fastener to provide a scratch fit. Fastening hole 150 is also partly defined by a ramped portion 156 projecting from the face of the implant to accommodate complete locking of the head of the fastener within fastening hole 150. In other embodiments, the implant may provide sufficient depth (i.e., be sufficiently thick) so as to not to require a ramped portion to achieve complete locking of the fastener at an angle within the implant.

Figure 21:
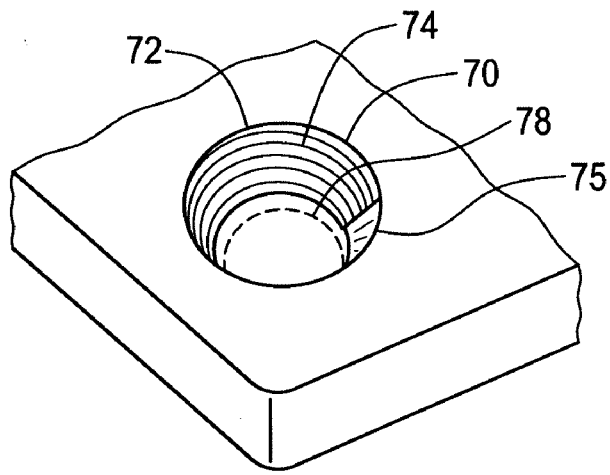
FIG. 21 is a perspective view of a fastening hole according to one embodiment of the invention.
Figure 22:
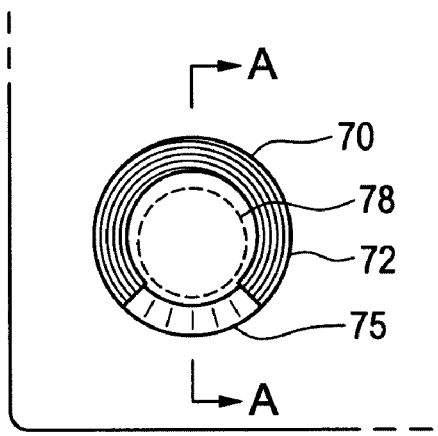
FIG. 22 is a top view of the fastening hole illustrated in FIG. 21.
Figure 23:
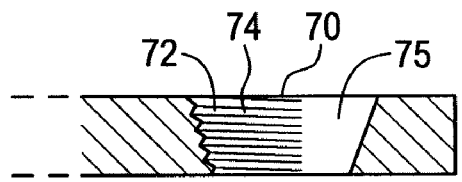
FIG. 23 is a side view along plane A-A in FIG. 22.

FIGS. 21 to 23 show fastening hole 70, an alternative embodiment of fastening holes 26, 26', 36, 36'. Fastening hole 70 is configured for "compression" locking of a fastener. Fastening hole 70 is frustoconical and has a threaded arc section 72 having internally spiralling threads 74 for receiving the threaded head of a fastener. Unlike fastening hole 50, fastening hole 70 has an unthreaded arc section 76 where internally spiralling threads 74 are absent. In some embodiments, such as the embodiment illustrated, the unthreaded arc section may extend from the proximal end to the distal end of fastening hole 70; in other embodiments, where the fastening hole is also frustoconical, the unthreaded arc section may only occupy a distal portion of an arc of fastening hole 70. Because internally spiralling threads 74 are absent at unthreaded arc section 76, the interior radius at the distal end of fastening hole 70 along unthreaded arc section 76 is slightly greater than the interior radius at the distal end of fastening hole 70 along threaded arc section 72 (as best shown in FIG. 22). Drill hole 78 is made in underlying bone before insertion of the fastener. Like drill hole 58, the diameter of drill hole 78 may be somewhat less than the diameter of the fastener to provide a scratch fit. The slightly greater interior radius of the distal end of fastening hole 70 along unthreaded arc section 76 allows for eccentric placement of drill hole 76. In particular, drill hole 78 is not centered with respect to fastening hole 70 and is instead shifted slightly toward unthreaded arc section 76 by, for example, 0.5 to 1.0 mm (as shown best in FIG. 22). As a result, as the fastener is being locked into fastening hole 70 (i.e., as the threaded head of the fastener is matingly received in the fastening hole 70), the elongated body of the fastener inserted into the bone acts as the resistance for levering the implant against underlying bone lying in the general direction of the unthreaded arc section 76.

Figure 24:
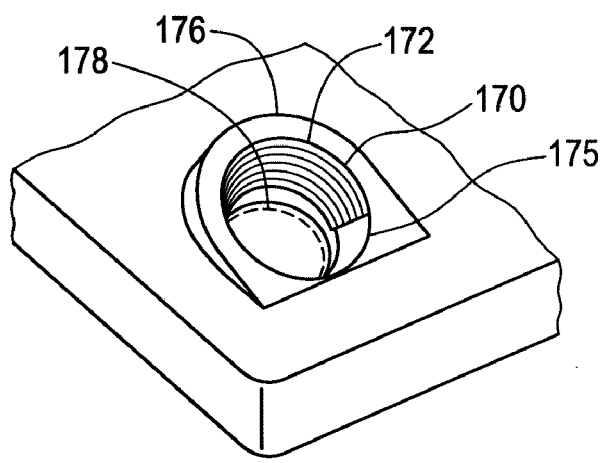
FIG. 24 is a perspective view of a fastening hole according to one embodiment of the invention.
Figure 25:
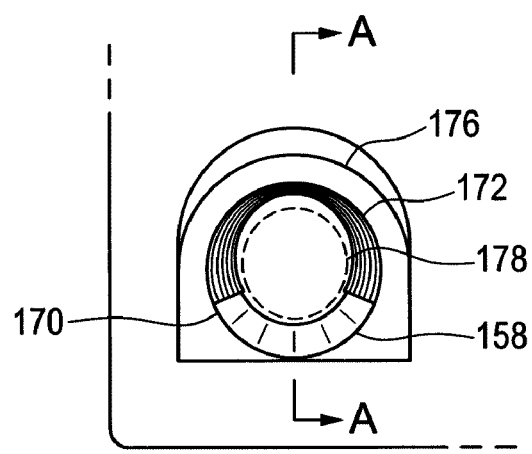
FIG. 25 is a top view of the fastening hole illustrated in FIG. 24.
Figure 26:
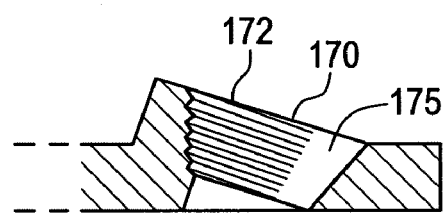
FIG. 26 is a side view along plane A-A in FIG. 25.

FIGS. 24 to 26 show fastening hole 170, an alternative embodiment of fastening holes 126, 126', 136, and 136'. Fastening hole 170 is configured for compression locking of a fastener at an acute angle to the face of the implant. Similar to fastening hole 150, fastening hole 170 has a ramped portion 176 to accommodate complete locking of a head of a fastener within fastening hole 170 at an angle. Otherwise, fastening hole 170 has features and functions analogous to fastening hole 70. For example, fastening hole 170 has a threaded arc section 172 with internally spiralling threads 174, an unthreaded arc section 176 where internally spiralling threads 174 are absent, and an eccentrically placed drill hole 178 having a diameter somewhat less than the diameter of the fastener to provide a scratch fit.

For compression locking of a talar implant, the unthreaded arc section may be provided on the anterior side of the fastening hole. As the fastener head is locked in to the fastening hole, the posterior extension of the implant is pulled slightly in an anterior direction against the posterior portion of the talus below the implant. The precise direction of the pulling force depends on the angle of insertion of the fastener. For talar implant 20 with flat fastening holes, the pulling force would be horizontal in the anterior direction for secure fixation. Even further secure fastening is achieved with talar implant 120 with angled fastening holes, wherein the pulling force would be at an angle, in a downward and anterior direction.

For compression locking with a tibial implant, the unthreaded arc section may be provided on the upper side of the fastening hole. As the fastener is locked in, the plate is pulled slightly in an upward direction against the bottom of the tibia. Again, the precise direction of the pulling force depends on the angle of insertion of the fastener. For tibial implant 30 with flat fastening holes, the pulling force would be directly upward for secure fixation. Even further secure fastening is achieved with tibial implant 130 with angled fastening holes, wherein the pulling force would be in an upward and anterior direction.

In other embodiments of the fastening holes, whether for neutral or compression locking, the fastening hole(s) and corresponding fastener head(s) may for example be unthreaded (e.g. for taper locking) rather than threaded, and/or cylindrical rather than frustoconical.

Figure 27A:
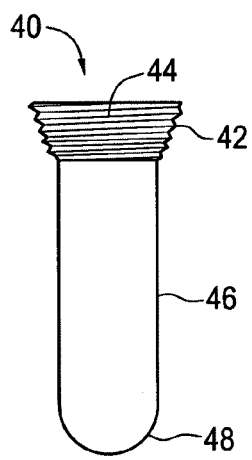
FIGS. 27A to 27C are side views of screw lock fasteners according to various embodiments of the invention.

Fasteners of the present invention, including fasteners 28, 28', 38, 38', 128, 128', 138, 138', 228, and 328 may be a peg, spike or the like of different shapes with different locking means such as a taper lock, barb lock, screw lock, expansion lock, secondary lock or any other known type of lock for forming a secure, locking connection between a fastener and a fastening hole. Fastener 40 shown in FIG. 27A is an example embodiment of a screw lock fastener. Fastener 40 has a head 42 having sides with externally spiralling threads 44. Head 42 may have a top (not shown) having a suitably shaped depression or protrusion for mating connection with a screwdriver, drill, or other means for locking fastener 40 into the fastening hole. Fastener 40 also has an unthreaded elongated body 46 that includes a rounded or hemispherical end portion 48. Body 46 has a smooth surface.

Figure 27B:
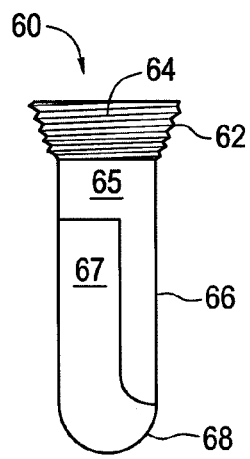

FIG. 27B shows fastener 60, another embodiment of a fastener with a screw lock. Fastener 60 is similar to fastener 40, with head 62 having sides with externally spiralling threads 64, and top of head 62 having features suitable for locking fastener 60 into the fastening hole. Unlike fastener 40, elongated body 66 of fastener 60 has at least one region with a smooth surface 65 and at least one region with a non-smooth surface 67. Non-smooth surface 67 may be any type of coating or surface treatment adaptable or suitable for ingrowth of boney tissue. Non-smooth surface 67 may for example be a porous surface formed by hydroxyapatite coating, cement coating, grit blasting or other known methods.

Smooth surface 65 may occupy a region encircling body 66 adjacent head 64 and a region extending along the length of elongated body 66 toward end portion 68. The remaining surface of body 66 may be occupied by non-smooth surface 67. In other embodiments, the elongated body of the fastener may have a different distribution of smooth and non-smooth surfaces, or may have a completely non-smooth surface.

When fastener 60 is in use with fastening holes such as fastening holes 70, 170 for compression locking, smooth surface 65 extending along elongated body 66 is aligned with and bears against the unthreaded arc section of the fastening hole during insertion. This alignment, which effectively shifts fastener 60 off center in the direction of the unthreaded arc section, in turn provides a small gap between the non-smooth surface 67 of fastener 60 and the distal end of the threaded arc section of the fastening hole. This small gap ensures minimal damaging contact to non-smooth surface 67 as fastener 60 glides through the fastening hole during insertion into bone.

Figure 27C:
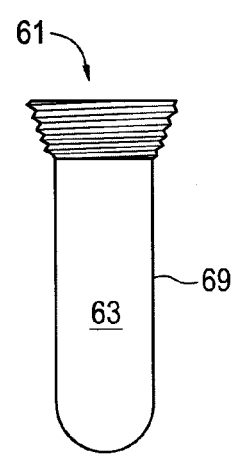

FIG. 27C shows fastener 61, a further embodiment of a fastener with a screw lock. Fastener 61 is identical to fastener 40 except that elongated body 69 has a completely non-smooth surface 63.

Figure 28A:
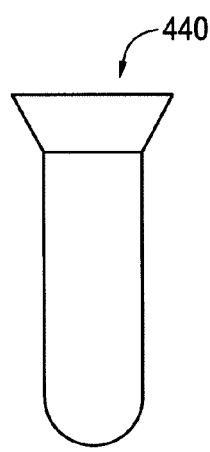
FIG. 28A to 28C are side views of taper lock fasteners according to various embodiments of the invention.
Figure 28B:
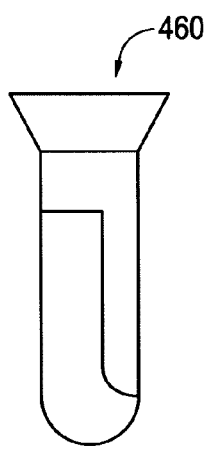
Figure 28C:
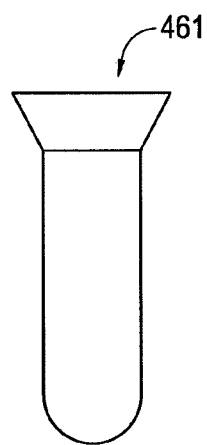

FIGS. 28A, 28B, and 28C show fasteners 440, 460, 461 which are identical in features and functions to fasteners 40, 60, 61 respectively except that fasteners 440, 460, 461 employ taper locks and therefore have non-threaded frustoconical heads.

The dimensions of the fasteners described herein may vary. For example, for the elongated body of the fasteners, the diameter may be 4 mm, and the length may range from 12 to 30 mm. The shape and size of the fastener head of the fasteners would be complementary to the shape and size of the corresponding fastener hole. The fasteners may be compatible with small or large fragment surgical instruments.

Figure 29:
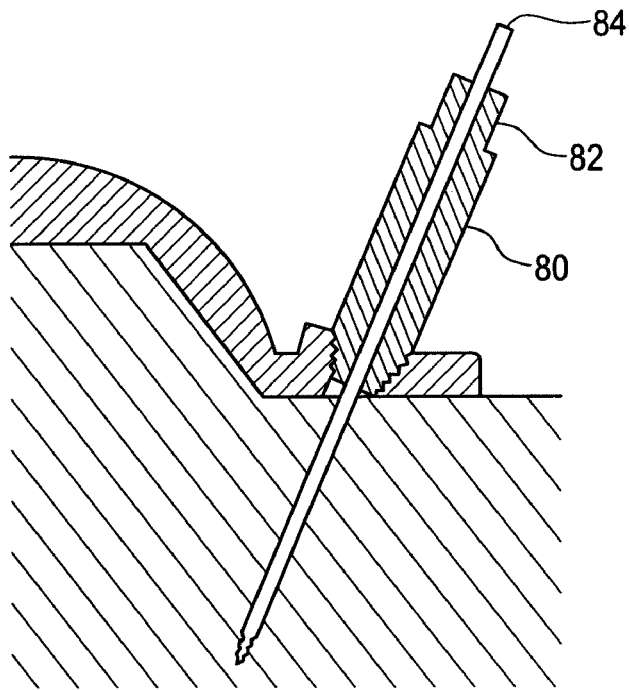
FIGS. 29 to 32 are cutaway side views illustrating the steps in fastening an implant to bone according to one embodiment of the invention.

The present invention avoids the use of a drilling template, and the problems associated therewith, by incorporating use of the final implant as part of the drilling jig. FIGS. 29 to 32 illustrate a jig for preparing a drill hole for neutral locking fastening of a talar implant to the talus bone according to an embodiment of the invention. In these figures, the talar implant may be talar implant 120, the fastening hole may be 50, 150, and the fastener may be 40, 60, for example. As shown in FIG. 29, a guide 80 with an externally threaded distal end is threaded into the fastening hole. Threaded guide 80 may for example be about 5 cm in length with a 2 mm longitudinal bore. A T-handle (not shown) may be connected to the proximal end 82 to assist in threading threaded guide 80 into the fastening hole. Guidewire 84 is then passed through threaded guide 80 and screwed or drilled into the bone. Guidewire 84 may for example be 2 mm in diameter.

Figure 30:
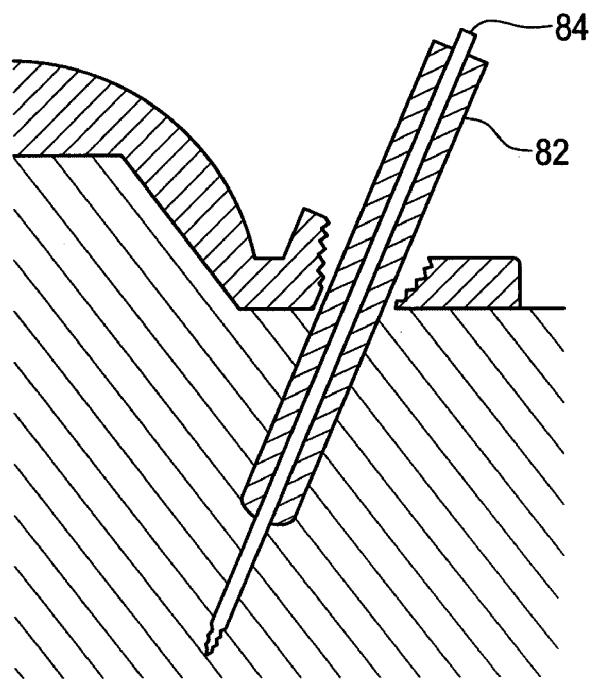
Figure 31:
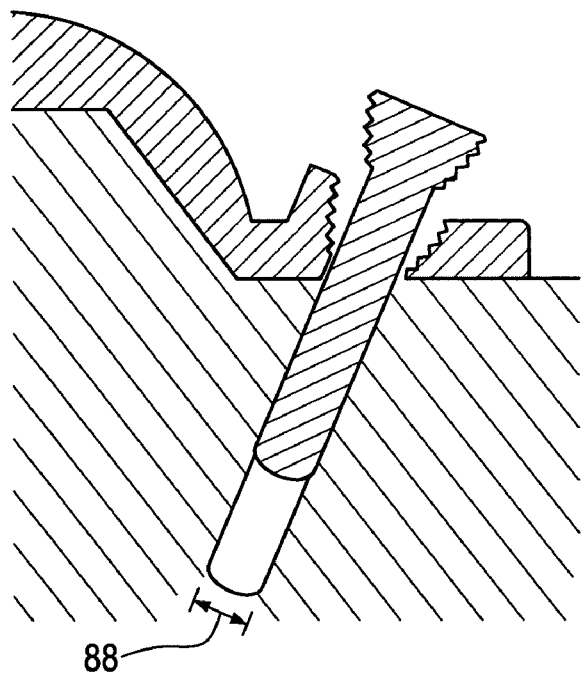
Figure 32:
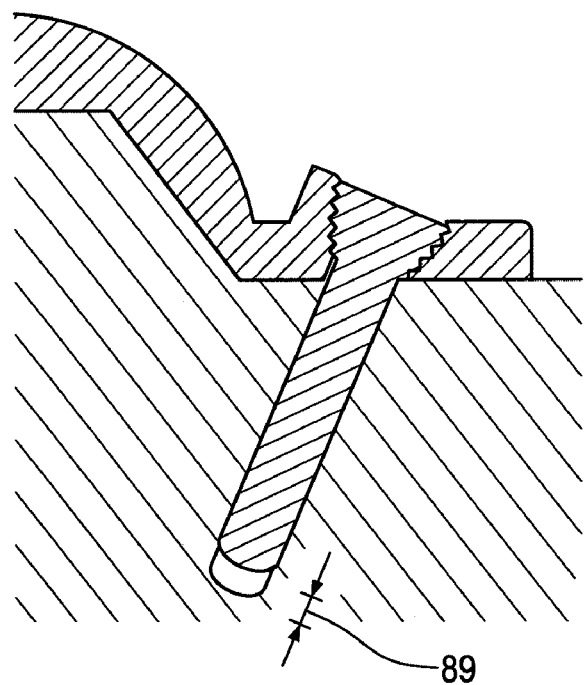

As shown in FIG. 30, threaded guide 80 is then removed, and a cannulated drill 86, guided by guidewire 84, is used to drill a hole into the bone. As shown in FIGS. 30 and 31 and mentioned above, drill 86 may drill a hole with a diameter 88 (e.g. 3.9 mm) slightly less than the diameter of the fastener's elongated body (e.g. 4.0 mm) to provide a scratch fit of the fastener. As shown in FIG. 32, the drill hole may be drilled deeper than the length of the fastener by an overdrill depth 89 to prevent the fastener from backing out of the drill hole over time. Overdrill depth 89 may, for example, be 4 to 6 mm. Since the implant is already in position (i.e., there is no need to remove a drilling template and replace it with the implant), the fastener may now be pushed or impacted in, and then locked in to the fastening hole with a screwdriver or drill, for example.

Similar steps as those illustrated in FIGS. 29 to 32 would be involved for drilling a fastener hole into a tibial bone for neutral locking of the fastener, for example for tibial implant 130 (not shown).

FIGS. 29 to 32 illustrate drilling for neutral locking with angled fastening; drilling for vertical/horizontal fastening (e.g. for implants 20, 30) may not require a threaded guide or guidewire and may instead be simply performed using an uncannulated drill and the fastening hole itself as a visual guide.

FIGS. 33 to 36 illustrate a jig for compression locking of a fastener according to an embodiment of the invention. Again, the use of a drilling template is avoided by adapting the actual prosthesis as a drilling guide. In these figures, the implant may be implant 20, 120, 220, 320, the fastening hole may be 70, 170, and the fastener may be 40, 60, for example. As shown in FIG. 33, a threaded guide 90 is threaded into the fastening hole, again optionally with the aid of a T-handle connected to the distal end of threaded guide 90. Threaded guide may for example be 4 cm in length with a 3 mm longitudinal bore. A cannula 92 with a guidewire 94 positioned in an eccentric longitudinal bore (as best shown in FIG. 33a) is slid into threaded guide 90. Cannula 92 may for example be 5 cm in length, 3 mm in outer diameter, and be provided with a handle at the proximal end. The eccentric positioning is such that the placement of the guidewire is shifted toward the unthreaded section of the fastening hole. Guidewire 94 is then screwed or drilled into the bone. In other embodiments, the longitudinal bore of the threaded guide, rather than the cannula, may be eccentric.

Figure 35:
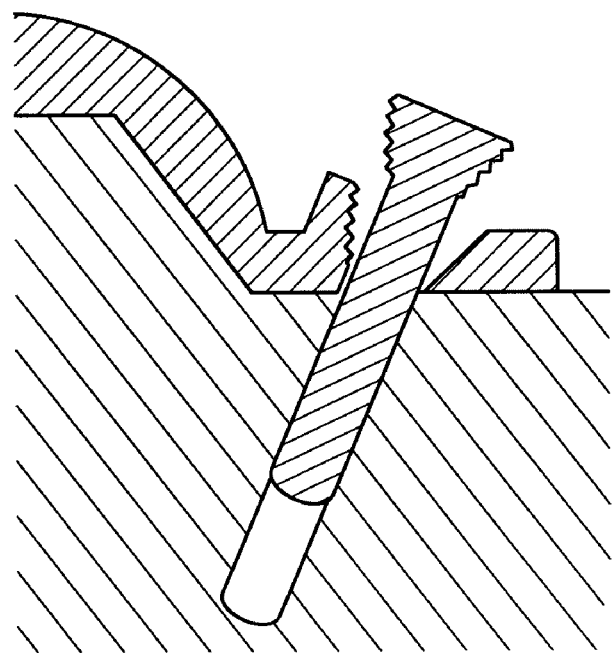
Figure 36:
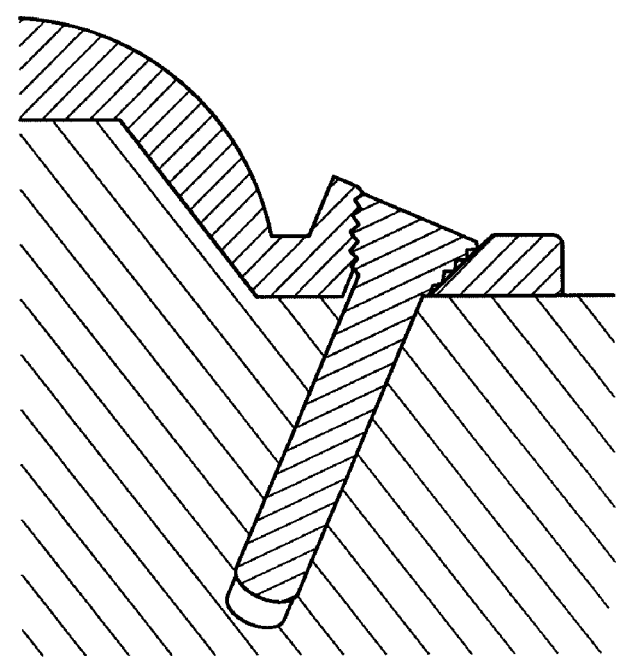

As shown in FIG. 34, threaded guide 90 and cannula 92 are then removed, and a cannulated drill 96, guided by guidewire 94, is used to drill a hole into the bone. As shown in FIG. 35, the resulting drill hole is shifted toward the unthreaded arc section of the fastening hole. Similar to the neutral locking option: the diameter of the drill hole 98 may be slightly less than the diameter of the fastener to provide a scratch fit; the drill hole may be drilled deeper than the length of the fastener by an overdrill depth 99 of for example 4 to 6 mm to ensure the fastener does not back out; and since the implant is already in position, the fastener may then be pushed or impacted in, and then locked in to the fastening hole with a screwdriver or drill.

Similar steps as those illustrated in FIGS. 33 to 36 would be involved for drilling a fastener hole into a tibial bone for compression locking of the fastener, for example for tibial implant 30, 130.

As will be apparent to those skilled in the art in the light of the foregoing disclosure, many alterations and modifications are possible in the practice of this invention without departing from the spirit or scope thereof. For example:

One, or more than two, fastening holes may be provided in each of the talar and tibial implants.

Fastening holes 50, 70, 150, 170, and the heads of fasteners 40, 60, may be cylindrical instead of frustoconical, but otherwise be identical to the fasteners and fastening holes described herein.

The fasteners and fastening holes may be completely unthreaded and lock by a taper lock resulting from the complementary frustoconical shape of the fastener heads (as shown in FIGS. 28A to 28C) and fastening holes. As the fastener would be impacted in for locking, no feature is necessary on the head of the fastener for mating connection with a screwdriver or drill. Otherwise, the taper locked fasteners and fastening holes are identical to the screw lock fasteners and fastening holes described herein. A taper locked fastener/fastening hole system may utilize neutral locking or compression locking as described herein. For example, for compression locking, the drill hole may be drilled eccentrically toward the side of the unthreaded fastening hole in which it is desired for the implant to be pulled.

The compression locking system described herein may be used in contexts of joints other than the ankle including knee, hip, shoulder, elbow and wrist.

The invention claimed is:

1. An ankle prosthesis comprising:
a talar implant comprising a body for mounting to a top of a talus, the body comprising at least one talar fastening hole;

a tibial implant comprising a plate for mounting to a bottom of a tibia;

a flange extending from the plate for bearing against an anterior surface of the tibia, the flange comprising at least one tibial fastening hole; and a plurality of fasteners for compression locking engagement with the at least one talar fastening hole and the at least one tibial fastening hole for fastening the talar implant and the tibial implant to the talus and the tibia respectively, each of the fasteners comprising locking means and an elongated unthreaded body;

wherein the at least one talar fastening hole and the at least one tibial fastening hole each comprise a distal end comprising:

a first arc section having a first radius; and a second arc section having a second radius greater than the first radius;

whereby the fastener is eccentrically insertable through the at least one talar fastening hole and the at least one tibial fastening hole, the eccentricity defined by a shift of the fastener toward the second arc section by a distance of up to the difference between the first and the second radii.

2. An ankle prostheses according to claim 1, wherein the second arc section is situated on an anterior side of the at least one talar fastening hole.

3. An ankle prostheses according to claim 1, wherein the second arc section is situated on an upper side of the at least one tibial fastening hole.

4. An ankle prosthesis according to claim 1, wherein the talar fastening holes are configured for vertical insertion of the fasteners and the tibial fastening holes are configured for horizontal insertion of the fasteners.

5. An ankle prosthesis according to claim 1, wherein the at least one talar fastening hole is configured for insertion of the fastener at an acute posterior angle and the at least one tibial fastening hole is configured for insertion of the fastener at an acute upward angle.

6. An ankle prosthesis according to claim 5, wherein the acute posterior angle is substantially the same as the angle at which a posterior component of the body extends downward from the horizontal.

7. An ankle prosthesis according to claim 1, wherein the first arc section comprises internal threads, the second arc section comprises an unthreaded section, and the locking means comprise external threads on a head of each fastener for screw locking of the fasteners to the at least one talar fastening hole and the at least one tibial fastening hole.

8. An ankle prosthesis according to claim 7, wherein the elongated unthreaded body of each of the fasteners comprises a smooth surface and a non-smooth surface, wherein the fastener is insertable with the smooth surface facing the unthreaded section.

9. An ankle prosthesis according to claim 1, wherein the at least one talar fastening hole and the at least one tibial fastening hole are frustoconical and the locking means comprise a frustoconical head for taper locking of each fastener to the at least one talar fastening hole and the at least one tibial fastening hole.

10. An ankle prosthesis according to claim 1, wherein the body of the talar implant comprises an anterior flange extending from the body for bearing against a neck of the talus.

11. An ankle prosthesis according to claim 10, wherein the anterior flange comprises the at least one talar fastening hole.

12. An ankle prosthesis according to claim 1, wherein the talar implant comprises an upper anterior surface comprising the at least one talar fastening hole.

13. An ankle prosthesis according to claim 1, comprising two talar fastening holes and two tibial fastening holes.

14. An ankle prosthesis according to claim 1, wherein the tibial fastening holes are configured for insertion of the fasteners in a direction parallel to the medial border of the tibia in the transverse plane.

* * * * *